(12) United States Patent
Leonov

(10) Patent No.: US 8,564,284 B2
(45) Date of Patent: Oct. 22, 2013

(54) FAULT DETECTION FOR LAMINATED CORE

(75) Inventor: Vladimir Leonov, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 286 days.

(21) Appl. No.: 13/025,260

(22) Filed: Feb. 11, 2011

(65) Prior Publication Data

US 2012/0206151 A1 Aug. 16, 2012

(51) Int. Cl.
  *G01B 7/06* (2006.01)
  *G01R 33/12* (2006.01)

(52) U.S. Cl.
  USPC ...... 324/230; 324/227; 324/511; 324/754.03; 324/243

(58) Field of Classification Search
  USPC ......... 324/164, 227–243, 500, 511, 537, 545, 324/546, 754.03
  See application file for complete search history.

(56) References Cited

U.S. PATENT DOCUMENTS

| | | | |
|---|---|---|---|
| 3,953,791 A * | 4/1976 | Spurr et al. | 324/200 |
| 4,996,486 A | 2/1991 | Posedel | |
| 5,321,362 A | 6/1994 | Fischer et al. | |
| 5,440,600 A | 8/1995 | Fanning | |
| 5,689,183 A | 11/1997 | Kohama | |
| 5,990,688 A | 11/1999 | Bourgeois et al. | |
| 6,040,694 A * | 3/2000 | Becker | 324/230 |
| 6,110,660 A * | 8/2000 | Kriz et al. | 435/4 |
| 6,469,504 B1 | 10/2002 | Kliman et al. | |
| 6,489,781 B1 | 12/2002 | Kliman et al. | |
| 6,756,788 B2 | 6/2004 | Kliman et al. | |
| 6,794,884 B2 | 9/2004 | Kliman et al. | |
| 6,815,957 B2 | 11/2004 | Hobelsberger et al. | |
| 6,873,152 B2 | 3/2005 | Kliman et al. | |
| 6,903,556 B2 | 6/2005 | Sutton | |
| 7,138,794 B1 * | 11/2006 | Cook et al. | 324/207.18 |
| 7,605,592 B2 | 10/2009 | Baca et al. | |
| 2003/0057961 A1 | 3/2003 | Hobelsberger et al. | |
| 2004/0000923 A1 | 1/2004 | Fischer et al. | |
| 2004/0124833 A1 | 7/2004 | Kliman et al. | |
| 2006/0219921 A1 | 10/2006 | Baca et al. | |
| 2009/0000138 A1 | 1/2009 | Rigby | |
| 2010/0141247 A1 * | 6/2010 | Candy | 324/239 |

FOREIGN PATENT DOCUMENTS

| | | |
|---|---|---|
| EP | 1318411 A2 | 6/2003 |
| GB | 2044936 A | 10/1980 |
| WO | 0210737 A2 | 2/2002 |

OTHER PUBLICATIONS

Vladimir Leonov; U.S. patent application entitled, "Fault Detection for Laminated Core."

* cited by examiner

*Primary Examiner* — Huy Q Phan
*Assistant Examiner* — Dustin Dickinson

(57) ABSTRACT

A method of evaluating the condition of a laminated core of an electric machine including positioning a magnetic flux injection excitation yoke extending between a pair of teeth of the laminated core, and the excitation yoke being wound with an excitation winding defining an electrical circuit for producing a magnetic flux excitation. Power is supplied to an excitation winding wound around the yoke to produce a magnetic flux in the yoke and to form a magnetic circuit through the yoke and the laminated core. A characteristic of the electrical circuit of the excitation winding is measured to identify a fault in the magnetic circuit corresponding to an eddy current between individual laminations in the laminated core.

20 Claims, 10 Drawing Sheets

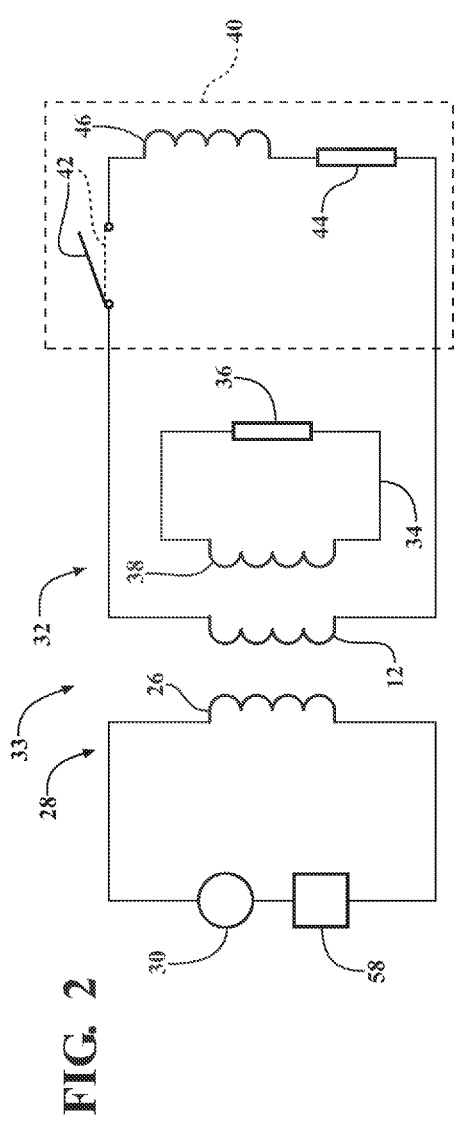
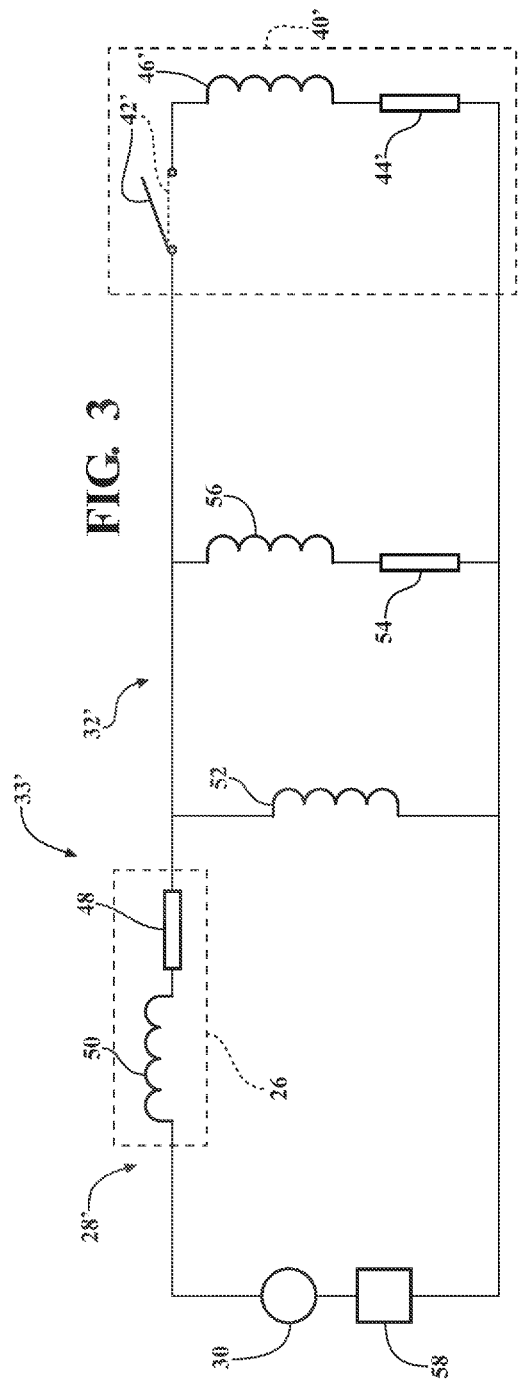

FAULT DETECTION FOR LAMINATED CORE

FIELD OF THE INVENTION

The present invention relates to fault detection for laminated cores and, more particularly, to detecting and locating faults caused by defects between laminations in a laminated core for an electric machine.

BACKGROUND OF THE INVENTION

Laminated stator cores, such as may be used in electric machines, may be formed by a plurality of laminations including a layer of insulating material located between adjacent laminations to prevent electrical conduction between the laminations. The laminated cores may be inspected for interlamination shorts during manufacture and during maintenance operations to identify conditions that may cause damage to the laminated core. The inspection operation may be performed using a measuring method comprising ring excitation of the stator lamination with a predetermined induction. This method, which indicates the effect of currents due to interlamination shorts by local temperature differences, requires a high-power and high-voltage source and excitation windings with large cross sections.

In another inspection technique, the laminated core may be provided with a special winding to excite magnetic flux in the overall core, and a low flux density is induced in the core. This inspection technique, known as an electromagnetic core imperfection detector (EL CID) test, provides a flux density in testing that is different than the flux density in operation of the electric machine, and may not provide sufficient flux to the laminated core teeth to provide a detection of insulation damage in the tooth area.

SUMMARY OF THE INVENTION

In accordance with an aspect of the invention, a method of evaluating the condition of a laminated core of an electric machine is provided. The method comprises positioning a magnetic flux injection excitation yoke extending between a pair of teeth of the laminated core, the excitation yoke having a pair of arms in engagement with the pair of teeth, and the excitation yoke being wound with an excitation winding for producing a magnetic flux excitation. Power is supplied to an electrical circuit defined by the excitation winding to produce a magnetic flux in the excitation yoke and to form a magnetic circuit through the excitation yoke and the laminated core. A characteristic of the electrical circuit of the excitation winding is measured to identify a fault in the magnetic circuit corresponding to an eddy current between individual laminations in the laminated core.

In accordance with another aspect of the invention, the measuring of the characteristic of the electrical circuit may include determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

In accordance with another aspect of the invention, the supplying power to the excitation winding may comprise providing power to the excitation winding at a constant voltage, and the measuring of the characteristic of the electrical circuit may include determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

In accordance with another aspect of the invention, the supplying power to the excitation winding may comprise providing power to the excitation winding at a constant current, and the measuring of the characteristic of the electrical circuit may include determining a variation in at least one of an impedance of the excitation winding and a voltage applied to the excitation winding corresponding to the fault in the magnetic circuit relative to a corresponding characteristic measured in the excitation winding for a magnetic circuit created through the excitation yoke and a portion of the laminated core without a fault.

In accordance with another aspect of the invention, the excitation yoke may include a second winding, and supplying power to the excitation winding may comprise measuring a voltage in the second winding corresponding to the magnetic flux in the excitation yoke and adjusting a voltage applied to the excitation winding with reference to the voltage in the second winding to maintain a constant magnetic flux in the excitation yoke.

In accordance with another aspect of the invention, in the case where a constant magnetic flux is maintained in the excitation yoke, the measuring of the characteristic of the electrical circuit may include determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

In accordance with another aspect of the invention, a reference element may be provided having an output characteristic corresponding to the measured characteristic of the excitation winding, and the characteristic of the excitation winding is compared to the output characteristic of the reference element to identify the fault in the magnetic circuit.

In accordance with another aspect of the invention, the electrical circuit of the excitation winding may comprise a bridge circuit in which the excitation winding and the reference element are each located in a respective branch of the bridge circuit.

In accordance with another aspect of the invention, the reference element may include a reference yoke wound with a reference winding, and the reference winding may be connected to the bridge circuit.

In accordance with another aspect of the invention, the reference yoke may be located a predetermined distance from the excitation yoke and may be moved along the laminated core with the excitation yoke to provide a fault indication at different locations along the laminated core.

In accordance with another aspect of the invention, the reference yoke may be located at a fixed location and may span between a pair of teeth of the laminated core at a location known to be free of defects between laminations of the laminated core to include the laminated core in a magnetic circuit of the reference yoke.

In accordance with another aspect of the invention, the reference yoke may be located in a magnetic circuit at a location spaced from the laminated core.

In accordance with another aspect of the invention, the reference element may include a capacitor.

In accordance with a further aspect of the invention, a method of evaluating the condition of a laminated core of an electric machine is provided. The method comprises positioning a magnetic flux injection excitation yoke extending between a pair of teeth of the laminated core, the excitation yoke having a pair of arms in engagement with the pair of teeth, and the excitation yoke being wound with an excitation winding for producing a magnetic flux excitation. A reference element is provided having an impedance that is substantially the same as an impedance of the excitation, and a bridge circuit is provided in which the excitation winding and the reference element are each located in a respective branch of the bridge circuit. Power is supplied to the excitation winding to produce a magnetic flux in the excitation yoke and to form a magnetic circuit through the excitation yoke and the laminated core, wherein one of a current and a voltage in the branches of the bridge circuit are balanced when the excitation yoke is positioned at a location where there are no faults in the laminated core. An imbalance is determined between the branches of the bridge circuit when at least one of the excitation yoke and the reference element is located adjacent to a fault formed by a short between adjacent laminations in the laminated core.

In accordance with a further aspect of the invention, the reference element may include a reference yoke wound with a reference winding, and the reference winding may be connected to the bridge circuit.

In accordance with a further aspect of the invention, the reference yoke may include a pair of arms located in engagement with a pair of teeth of the laminated core to form a magnetic circuit through the reference yoke and the laminated core.

In accordance with a further aspect of the invention, the reference yoke may be located in a magnetic circuit separate from the laminated core.

In accordance with a further aspect of the invention, the bridge circuit may comprise a Maxwell-Wein bridge circuit and the reference element may include a capacitor providing a capacitive impedance balanced against an inductance of the excitation coil.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 2 is a schematic view illustrating an equivalent circuit for the apparatus illustrated in FIG. 1A;

FIG. 3 is a schematic view illustrating an alternative equivalent circuit for the apparatus illustrated in FIG. 1A;

DETAILED DESCRIPTION OF THE INVENTION

In the following detailed description of the preferred embodiment, reference is made to the accompanying drawings that form a part hereof, and in which is shown by way of illustration, and not by way of limitation, specific preferred embodiments in which the invention may be practiced. It is to be understood that other embodiments may be utilized and that changes may be made without departing from the spirit and scope of the present invention.

Figure 1A:
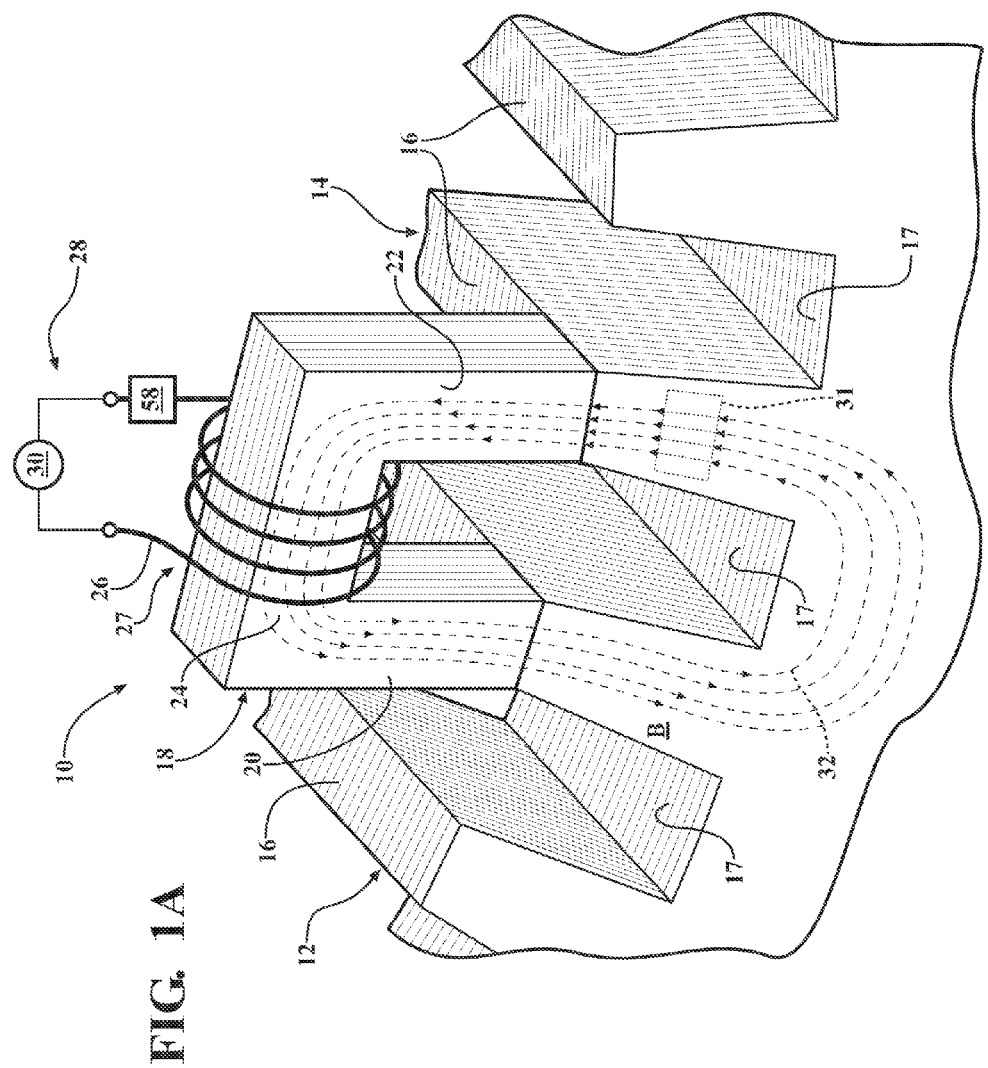
FIG. 1A is a perspective view of an apparatus for evaluating the condition of a laminated core in accordance with the present invention.

Referring to FIG. 1A, an apparatus 10 is illustrated for evaluating the condition of the magnetic circuit of a laminated core 12 of an electric machine, such as a laminated stator core in a generator. The laminated core 12 may comprise an assembly of superimposed laminations of magnetic material, each coated with an electrically insulating material to form, for example, a stator having a face 14 defined by a plurality of spaced apart radially projecting teeth 16, and associated slots 17 located between the teeth 16. As is described further below, the apparatus 10 may be used to detect faults, such as may be caused by defects in the insulating material between laminations, and resulting electrical shorts between adjacent laminations, as indicated by a variation in the magnetic flux conducted through the magnetic circuit passing through the teeth 16 relative to the magnetic flux conducted through a magnetic circuit formed by the teeth 16 at a different location, i.e., at a location defined by a portion of the laminated core 12 that does not have a fault.

The apparatus 10 includes an excitation yoke 18 comprising a U-shaped ferromagnetic member, which may comprise a plurality of laminated sheets, and including a pair of arms 20, 22 connected by a transverse portion 24. The transverse portion 24 of the excitation yoke 18 is wound with a magnetic flux generating excitation winding 26. The excitation yoke 18 and winding 26 form a probe structure 27 for generating a magnetic flux in the laminated core 12. During a testing procedure for evaluating the condition of the laminated core 12, the yoke 18 is positioned with the arms 20, 22 in close proximity to a pair of the laminated core teeth 16, wherein ends of the arms 20, 22 are preferably located at a spacing matching the spacing of the pair of teeth 16 and any air gap between the arms 20, 22 and the teeth 16 is preferably kept to a minimum. An alternating voltage or current is provided to an electrical excitation circuit 28 comprising the winding 26 to produce a magnetic flux in the yoke 18 and to inject a magnetic flux excitation into the laminated core 12. The excitation circuit 28 may include a power source 30, i.e., a voltage or current source, which may provide an alternating voltage or current at a frequency of 50 or 60 Hz, or may operate at a predetermined frequency from 60 Hz to 800 Hz. The magnet flux is generated in a local area of the laminated core 12 length located near the pair of teeth 16 spanned by the yoke 18. The magnetic flux density generated by the yoke 18 is preferably the same as or comparable to the magnetic flux density generated in the laminated core 12 during operation of the electric machine, such as during use of the laminated core 12 in an electrical generator.

The magnetic circuit of the yoke 18 is coupled with a magnetic circuit 32 of a test zone of the laminated core 12, and the two coupled magnetic circuits form a coupled magnetic test circuit 33 (FIG. 2). An alternating current provided to the winding 26 is limited by an impedance of the winding 26 in association with the yoke 18 that has active and reactive components. Referring to FIG. 2, illustrating an equivalent circuit for the test zone magnetic circuit 32 and associated excitation circuit 28 of the coupled magnetic test circuit 33, the current in the winding 26 has a flux linkage with eddy currents in the laminated core 12 through the yoke 18, where the effects of eddy currents in the individual laminations are represented by circuit portion 34 having an equivalent resistance 36 and leakage inductance 38. In addition, in the case where shorts or faults exist between adjacent laminations, such as where insulation is missing between laminations, as depicted at 31 in FIGS. 1A and 1B, the flux linkage with the winding 26 may include circulating currents formed by the shorts in the laminated core 12, as illustrated by circuit portion 40. A short between laminations is represented by the switch 42 being located in the closed position (represented by dotted line) to include an equivalent resistance 44 and inductance 46 in the test zone magnetic circuit 32. The equivalent resistance 44 may represent or correspond to circulating currents passing through the shorts between the laminations, and the equivalent inductance 46 may represent or correspond to leakage inductance of circulating currents passing through the shorts between the laminations.

FIG. 3 illustrates an equivalent electrical circuit 33' similar to an equivalent circuit of a transformer that includes a test zone portion 32' and associated excitation circuit portion 28'. The excitation circuit portion 28' includes a winding 26 represented by a resistance 48, a mutual inductance 52, and a leakage inductance 50. The mutual inductance 52 is further included in the test zone portion 32', wherein the mutual inductance 52 represents the mutual inductance between the winding 26 and 1) eddy currents in the laminations; and 2) circulating currents through shorts between laminations. An inductance 56 represents leakage inductance of eddy currents within the individual laminations, and a resistor 54 represents an equivalent resistance of eddy currents within the individual laminations. In addition, in the case where shorts or faults exist between adjacent laminations in the test zone circuit portion 32', the flux linkage with the winding 26 may include circulating currents formed by the shorts in the laminated core 12, as illustrated by circuit portion 40'. A short between laminations is represented by the switch 42' located in the closed position (represented by dotted line) to include an equivalent resistance 44' and inductance 46' in the test zone circuit 32'. The equivalent resistance 44' limits circulating currents passing through the shorts between the laminations, and the equivalent inductance 46' represents leakage inductance of circulating currents passing through the shorts between the laminations.

As illustrated by the equivalent circuits of FIGS. 2 and 3, the current in the winding 26 and its impedance at a fixed or predetermined voltage may vary depending on the flux linkage of the winding 26 to itself (self inductance), the value of eddy currents in individual laminations linked with the magnetic flux through the winding 26 (represented by 36 and 38 in FIG. 2; and 52, 54, 56 in FIG. 3), and circulating currents between laminations linked with the magnetic flux through the winding 26 (represented by 44, 46 in FIG. 2; and 44', 46' in FIG. 3). If the yoke 18 and associated winding 26 are moved longitudinally along the laminated core 12, i.e., along the lengthwise direction of the teeth 16, a characteristic of the electrical circuit 28 of the excitation winding 26 may vary.

Hence, different characteristics or parameters may be used or monitored as an indicator of faults or shorts between the laminations. For example, in the case that the power supply 30 is operated without special stabilization, i.e., without additional components to stabilize or compensate for small variations from a predetermined voltage or current, a monitoring module 58 associated with the excitation circuit 28 may monitor either the current in the winding 26 or the impedance of the winding 26 as an indicator of a lamination short. Similarly, in a case where the power source 30 is a constant voltage power source, i.e., with stabilized voltage, the monitoring module 58 may also monitor either the current in the winding 26 or the impedance of the winding 26 as an indicator of a lamination short. In a case where the power source 30 is a constant current power source, i.e., with stabilized current, the monitoring module 58 may monitor either a voltage applied to the winding 26 or the impedance of the winding 26 as an indicator of a lamination short.

Figure 1B:
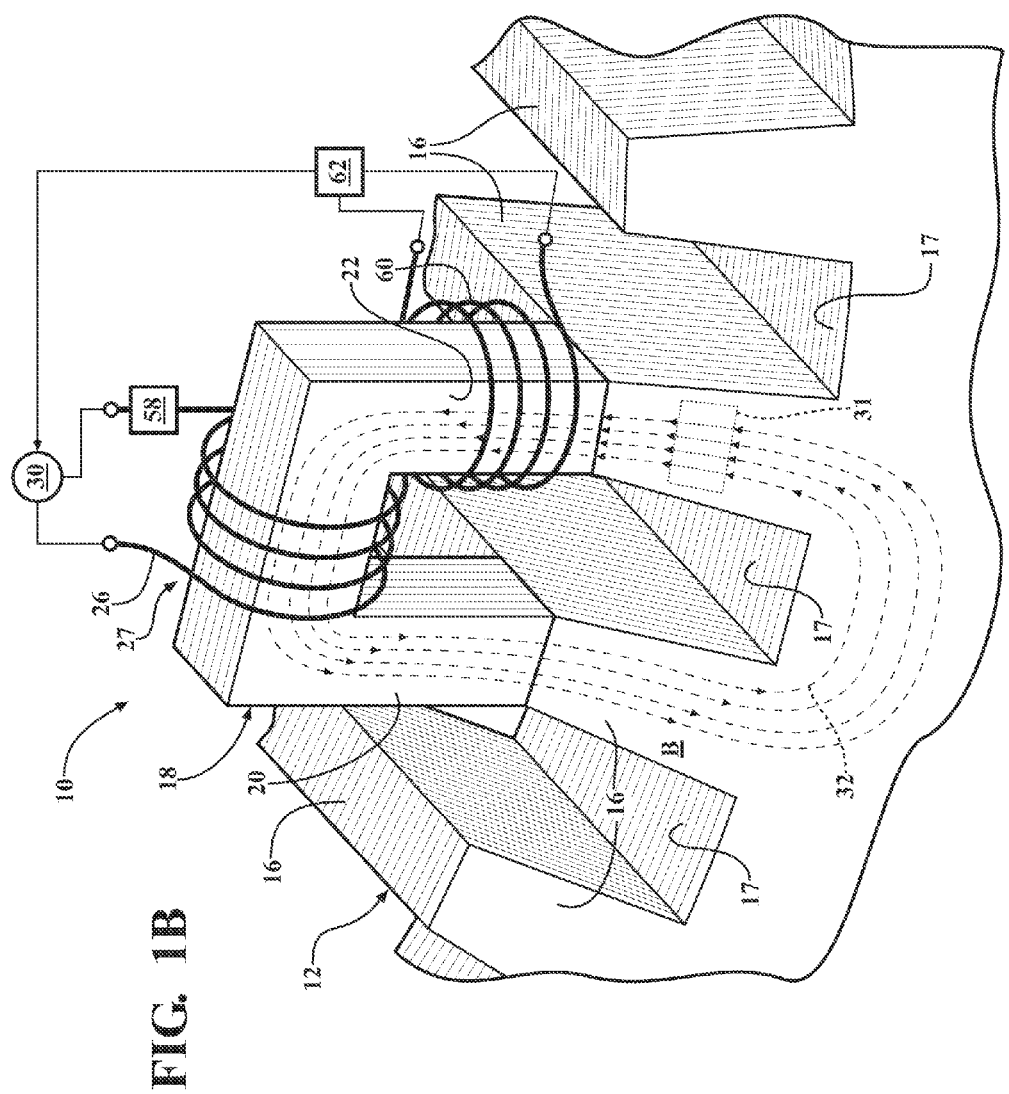
FIG. 1B is a perspective view illustrating a further aspect for the apparatus for evaluating the condition of a laminated core in accordance with the present invention.
Figure 4:
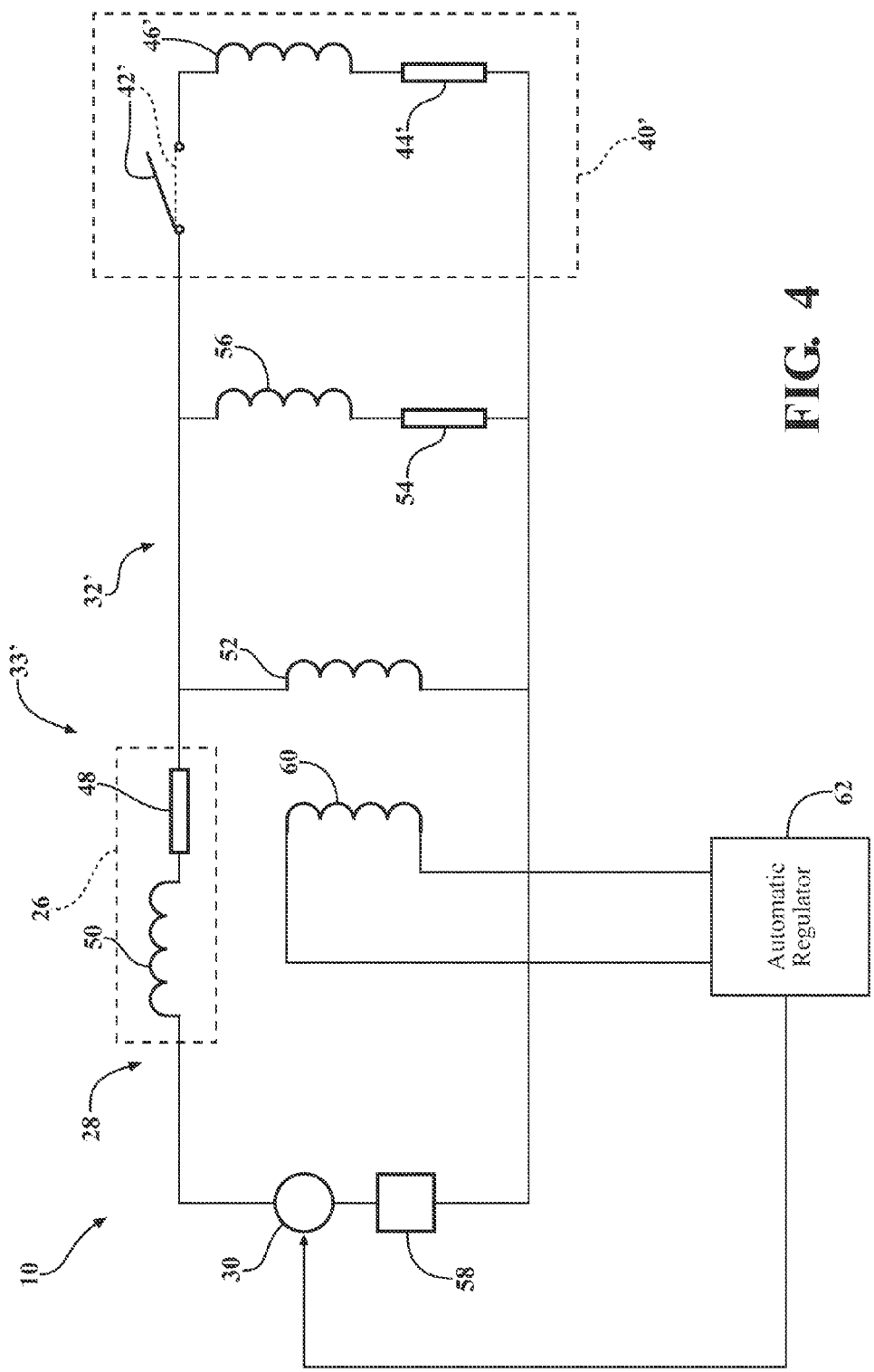
FIG. 4 is a schematic view illustrating an equivalent circuit for the apparatus illustrated in FIG. 1B.

In accordance with a further aspect of the apparatus 10, the power source 30 may be controlled such that a constant flux is maintained in the yoke 18. Referring to FIGS. 1B and 4, where FIG. 4 illustrates a modified form of the equivalent circuit of FIG. 3, the yoke 18 may be provided with a second winding 60 connected to a regulator 62 for controlling a voltage output of the power supply 30. The magnetic flux in the yoke 18 generates an AC voltage in the second winding 60 that is proportional to the magnetic flux in the yoke 18. The regulator 62 monitors the output AC voltage of the second winding 60 to automatically control the output voltage of the power source 30 so as to maintain the magnetic flux in the yoke 18 substantially constant. In accordance with this configuration of the apparatus 10, the monitoring module 58 may monitor either a current in the winding 26 or the impedance of the winding 26 as an indicator of a lamination short.

In each of the above described configurations for detecting a fault in the laminated core 12, the monitored parameter (current, impedance or voltage) may be compared to known values corresponding to a laminated core known to be without faults. The monitoring module 58 may provide a direct indication of the monitored parameter, such as by a meter or other read-out device. Alternatively, or in addition, the monitoring module 58 may digitize the results received as an indicator of a fault in the laminated core 12, such as by means of a microprocessor included in the monitoring module 58, and store the digitized results in a memory for automated processing and analysis to identify fault locations in the laminated core 12.

Figure 5:
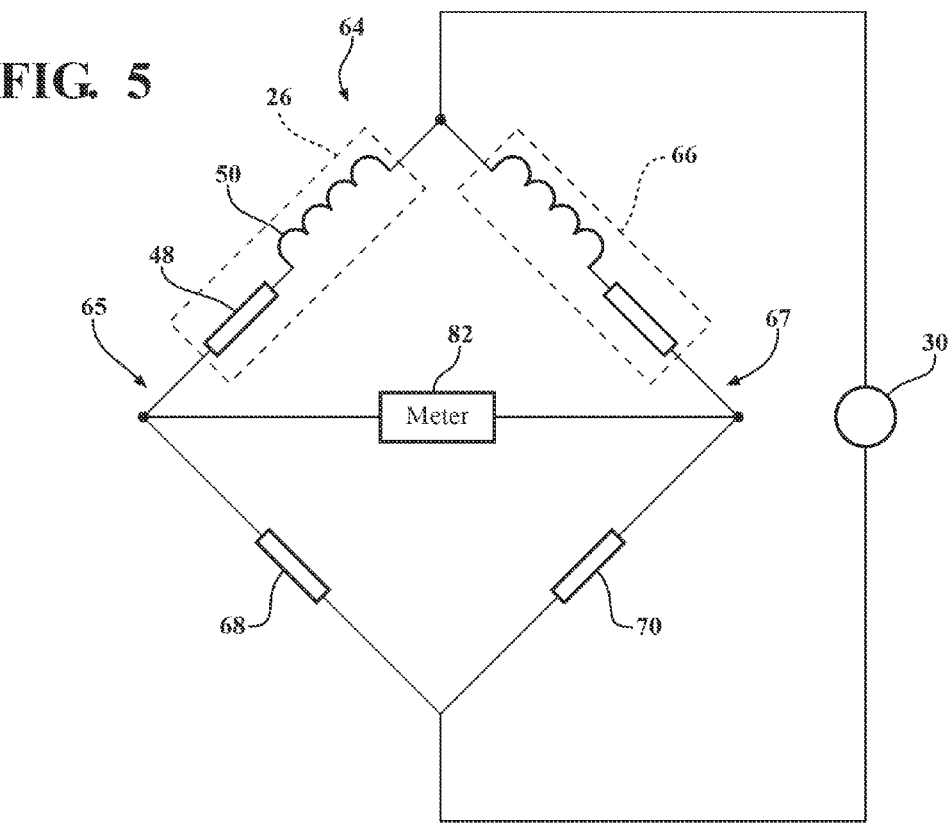
FIG. 5 is a schematic view illustrating a bridge circuit for evaluating the condition of a laminated core with reference to a reference element.
Figure 6A:
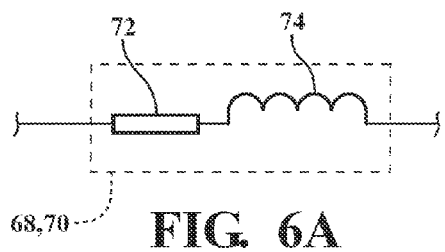
FIGS. 6A-C are schematic views illustrating alternative arm elements for use in a bridge circuit for evaluating the condition of a laminated core.
Figure 6B:
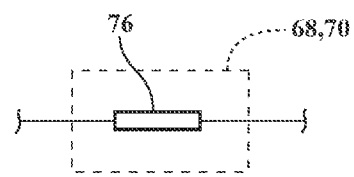
Figure 6C:
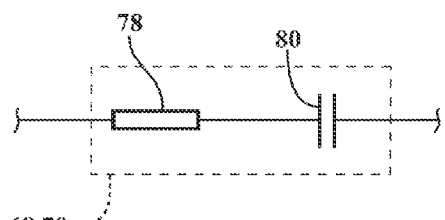

In accordance with a further aspect of the present apparatus 10, a configuration for identifying an indicator value corresponding to a fault in the laminated core 12 is shown in FIG. 5. In particular, a configuration for determining a value received at the monitoring module 58 relative to a reference value in a bridge circuit 64 is shown. The configuration including the bridge circuit 64 may include a first upper arm defined by the portion of the excitation circuit 28 including the probe structure 27 (excitation yoke 18 and winding 26), as described with reference to FIGS. 1A and 1B. The bridge circuit 64 may further include a second upper arm defined by a reference element 66 which may comprise, for example, one of a reference winding, a reference inductance or a reference capacitance, as is described further below. First and second lower arms 68, 70 of the bridge circuit 64 may comprise identical elements including, for example, a resistor 72 and inductor 74 (FIG. 6A), resistor(s) 76 (FIG. 6B), or a resistor 78 and capacitor 80 (FIG. 6C). It should be noted that the resistor 72 and inductor 74 of FIG. 6A may be connected either in series or in parallel, and the resistor 78 and capacitor 80 of FIG. 6C may be connected either in series or parallel.

The first upper arm defined by the probe structure 27 and the first lower arm 68 define a first branch 65 of the bridge circuit 64, and the second upper arm defined by the reference element 66 and the second lower arm 70 define a second branch 67 of the bridge circuit 64. A meter 82 may be provided, spanning between the two branches 65, 67 of the bridge circuit 64, to provide an indication of a current or voltage difference between the two branches 65, 67. The meter 82 may comprise an operator readable meter and/or may comprise circuitry of the monitoring module 58 to provide an analog or digital measurement indicative of a voltage difference or a current difference between the current or voltage in the two branches 65, 67. In addition to the monitoring module 58 including the voltage or current measuring component of the bridge circuit 64 represented by the meter 82, the monitoring module 58 may comprise one or more additional components of the bridge circuit 64 such as, for example, the lower arms 68, 70 and/or the reference element 66 of the bridge circuit 64.

Figure 8A:
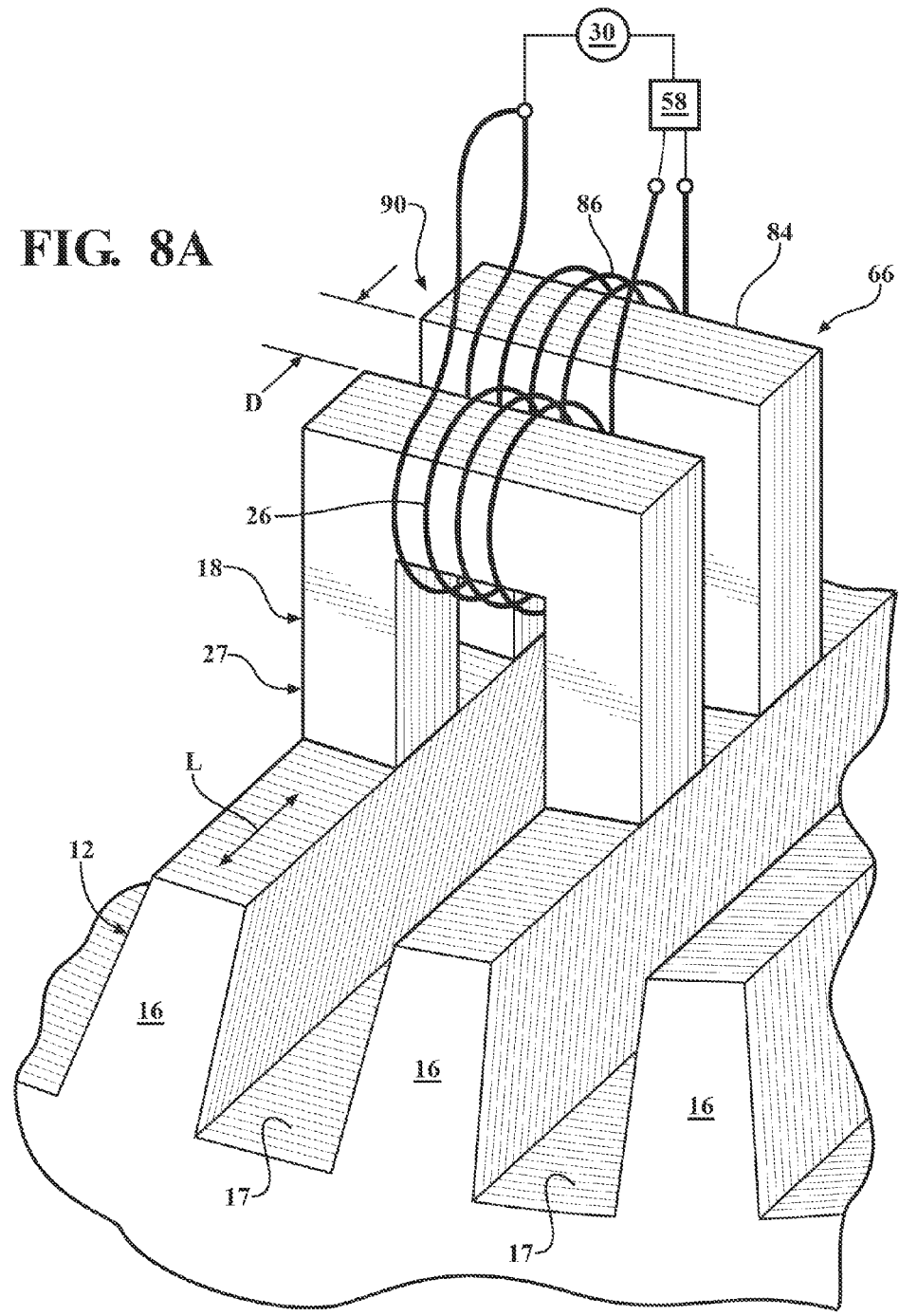
FIGS. 8A-C are perspective views of alternative configurations for an apparatus including a reference element for evaluating the condition of a laminated core in accordance with the present invention.

FIG. 8A illustrates an exemplary configuration for the reference element 66, where the reference element 66 comprises a reference yoke 84 wound with a reference winding 86, and where the second upper arm of the bridge circuit 64 may comprise the reference winding 86 (FIG. 6) and the laminated core 12 is included as part of the magnetic circuit of the reference element 66. The reference winding 86 may be connected to the power supply 30, where the power supply 30 provides a power output to the reference winding 86 comprising a substantially identical current and/or voltage to that output by the power source 30 to the excitation winding 26. The reference yoke 84 and reference winding 86 preferably comprise elements that are substantially identical to the excitation yoke 18 and excitation winding 26, respectively, such that the reference yoke 84 and reference winding 86 will exhibit a substantially identical impedance, i.e., substantially identical resistance and substantially identical reactance, to the impedance of the excitation yoke 18 and excitation winding 26 under identical conditions. That is, when both the probe structure 27 and the reference element 66 are positioned at locations along the laminated core 12 where there are no lamination shorts, the meter 82 of the bridge circuit 64 will detect a voltage or current difference between the two bridge circuit branches 65, 67 that is close to zero. If the probe structure 27 is located near a lamination short 31 (FIG. 1A), such that a circulating flux is generated, the impedance of the winding 26 will change, creating an imbalance in the bridge circuit 64. The imbalance in the bridge circuit 64 may be detected by the meter 82 as an increase in voltage or current, providing an indication of the presence of the lamination short.

In accordance with one aspect of the reference element 66, as described above with reference to FIG. 8A, the probe structure 27 may define a first probe, and the reference element 66 may define a second probe connected or supported for movement with the probe structure 27 and spaced a predetermined distance, d, from the probe structure 27. The connected probe structure 27 and reference element 66 form a probe assembly 90. The power from the power sources 30 is connected to the windings 26 and 86 such that the windings 26 and 86 create a magnetic flux of the same polarity on the common or same teeth 16 of the laminated core 12, assuming the windings 26 and 86 operate with the same impedance. In addition, the distance, d, between the probe structure 27 and the reference structure 66 is preferably great enough to avoid a significant flux linkage between the windings 26 and 86, in the event that an impedance difference were to occur in the windings 26 and 86. During an inspection operation, the probe assembly 90 may be moved along the longitudinal direction, L, of the laminated core 12. When either the probe structure 27 or the reference element 66 encounters a short in the laminations of the laminated core 12, the impedance of the respective winding 26, 86 adjacent to the lamination short will change relative to the impedance of the other winding 26, 86, changing the balance in the bridge circuit 64, as may be indicated by a change in current or voltage on the meter 82.

Figure 8B:
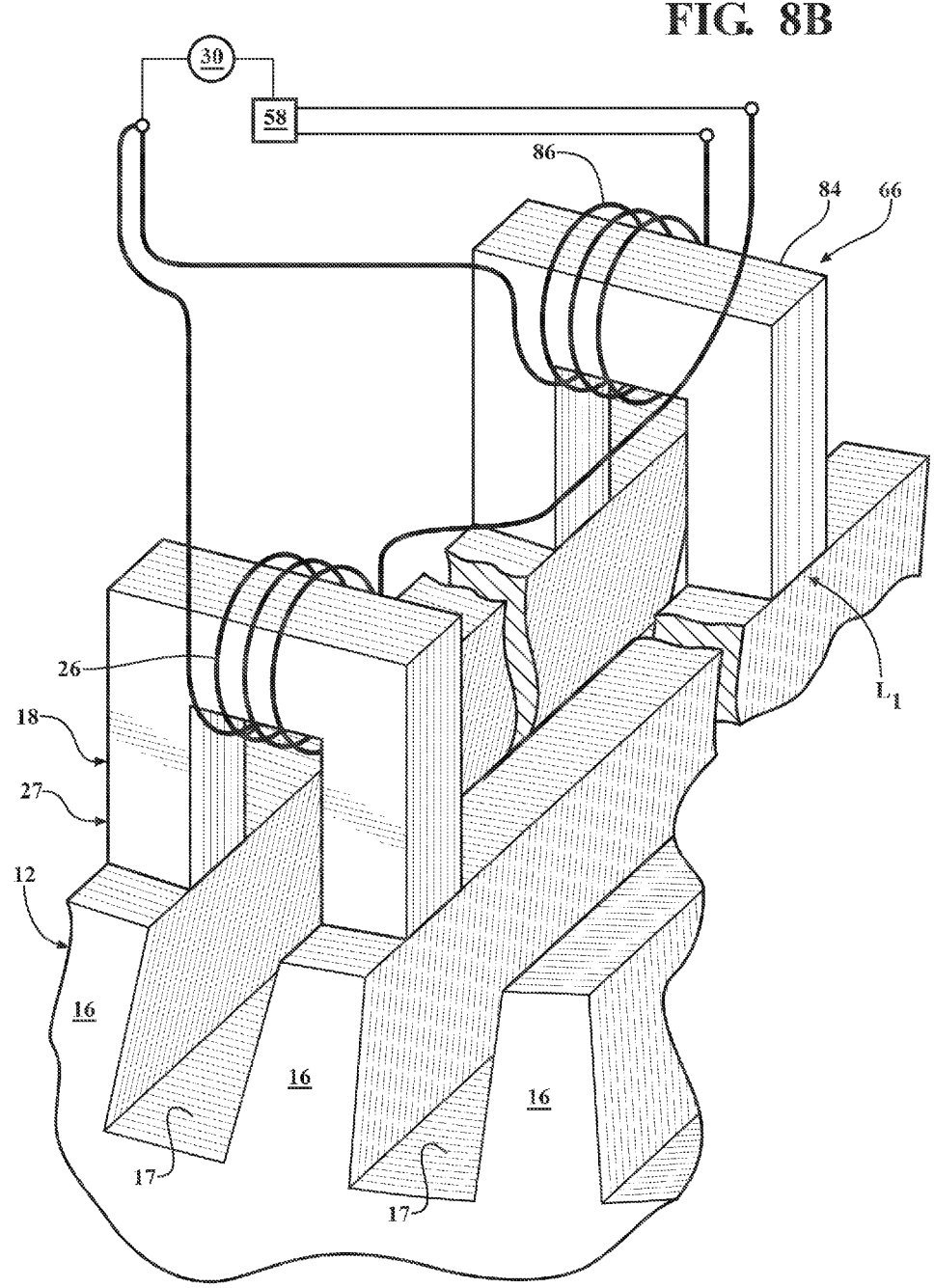

In accordance with another aspect of the reference element 66, as described above with reference to FIG. 5, the probe structure 27 and reference element 66 may be substantially identical structures, such as is described above with regard to the reference yoke 84 and reference winding 86 (FIG. 8A). However, as illustrated in FIG. 8B, the reference structure 66 may be positioned at a stationary location $L_1$ on the laminated core 12 with the reference yoke 84 extending between a pair of teeth 16, such that the laminated core 12 forms part of the magnetic circuit of the reference element 66. The stationary location $L_1$ is selected to be at a portion of the laminated core 12 that is known to be free of faults or shorts between laminations. Further, the construction of the reference element 66 and its location $L_1$ on the laminated core 12 is such that the reference element 66 will exhibit an impedance which is substantially identical to that of the probe structure 27 when the probe structure 27 is positioned at a location along the laminated core 12 where there are no lamination shorts. The probe structure 27 may be moved along the laminated core 12 in the longitudinal direction, L, to detect shorts between the laminations. When the probe structure 27 encounters a short 31 (FIG. 1A) in the laminations of the laminated core 12, the impedance of the winding 26 will change relative to the impedance of the reference winding 86, changing the balance in the bridge circuit 64, as may be detected at the monitoring module 58, i.e., as may be indicated by a change in current or voltage on the meter 82.

Figure 8C:
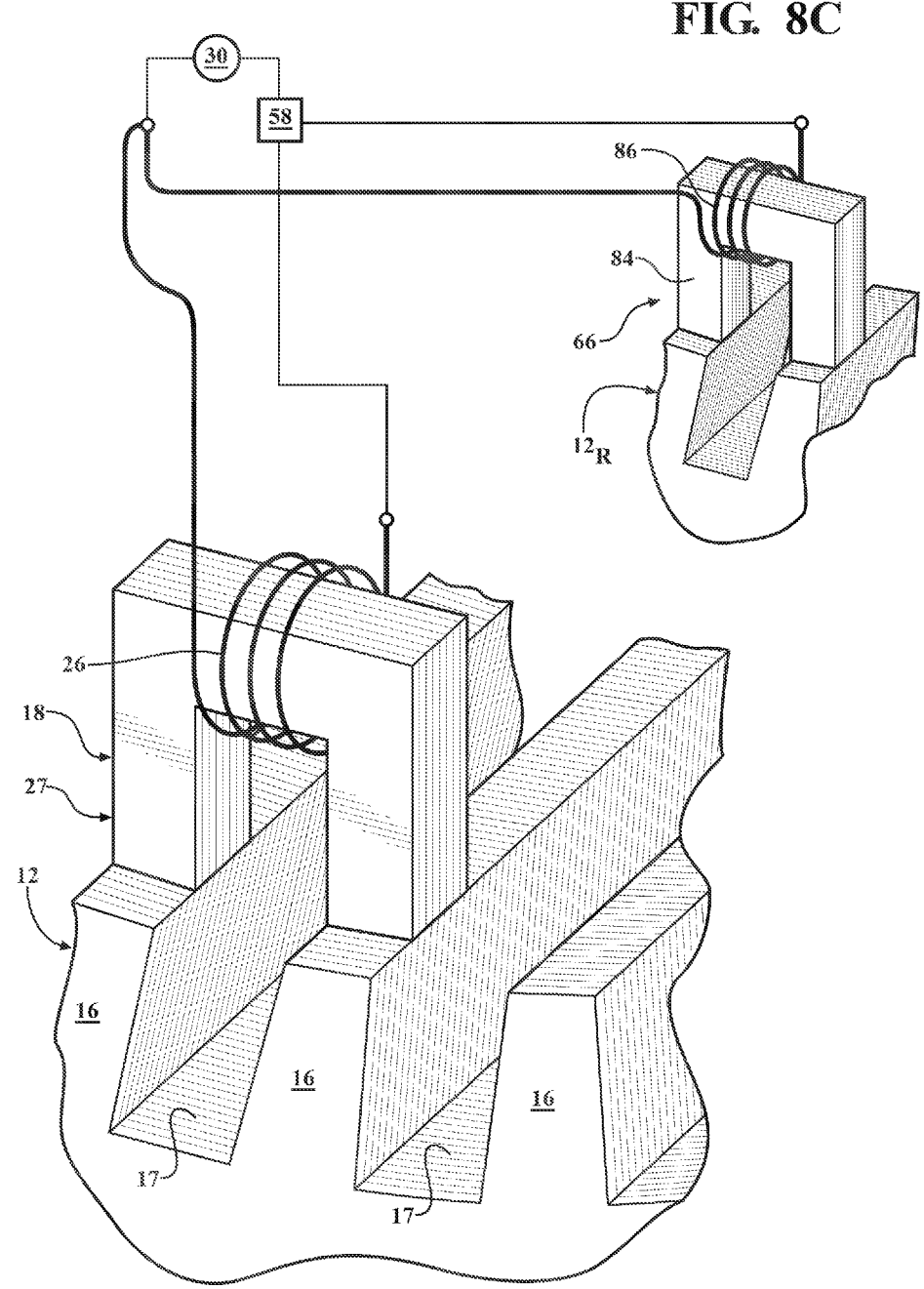

In accordance with a further aspect of the reference element 66, as described above with reference to FIG. 5, the reference element 66 may be located in spaced relation from the laminated structure 12, such that the laminated structure 12 is not part of a magnetic circuit of the reference element 66. As illustrated in FIG. 8C, the reference element 66 may comprise a reference yoke 84 and reference winding 86 similar to that described above with reference to FIG. 8A and may be associated with a reference magnetic circuit $12_R$, or may comprise a different structure including a reference winding 86 forming a magnetic circuit separate from the laminated core 12, and may be energized by the power source 30. The winding 86 of the reference structure 66 may be constructed to have the same inductance and impedance, or may have only the same impedance, as the winding 26 of the probe structure 27. In accordance with this aspect, the probe structure 27 may be moved along the laminated core 12 in the longitudinal direction, L, to detect shorts between the laminations. When the probe structure 27 encounters a short 31 (FIG. 1A) in the laminations of the laminated core 12, the impedance of the winding 26 will change relative to the impedance of the reference winding 86, changing the balance in the bridge circuit 64, as may be detected at the monitoring module 58, i.e., as may be indicated by a change in current or voltage on the meter 82.

Figure 7:
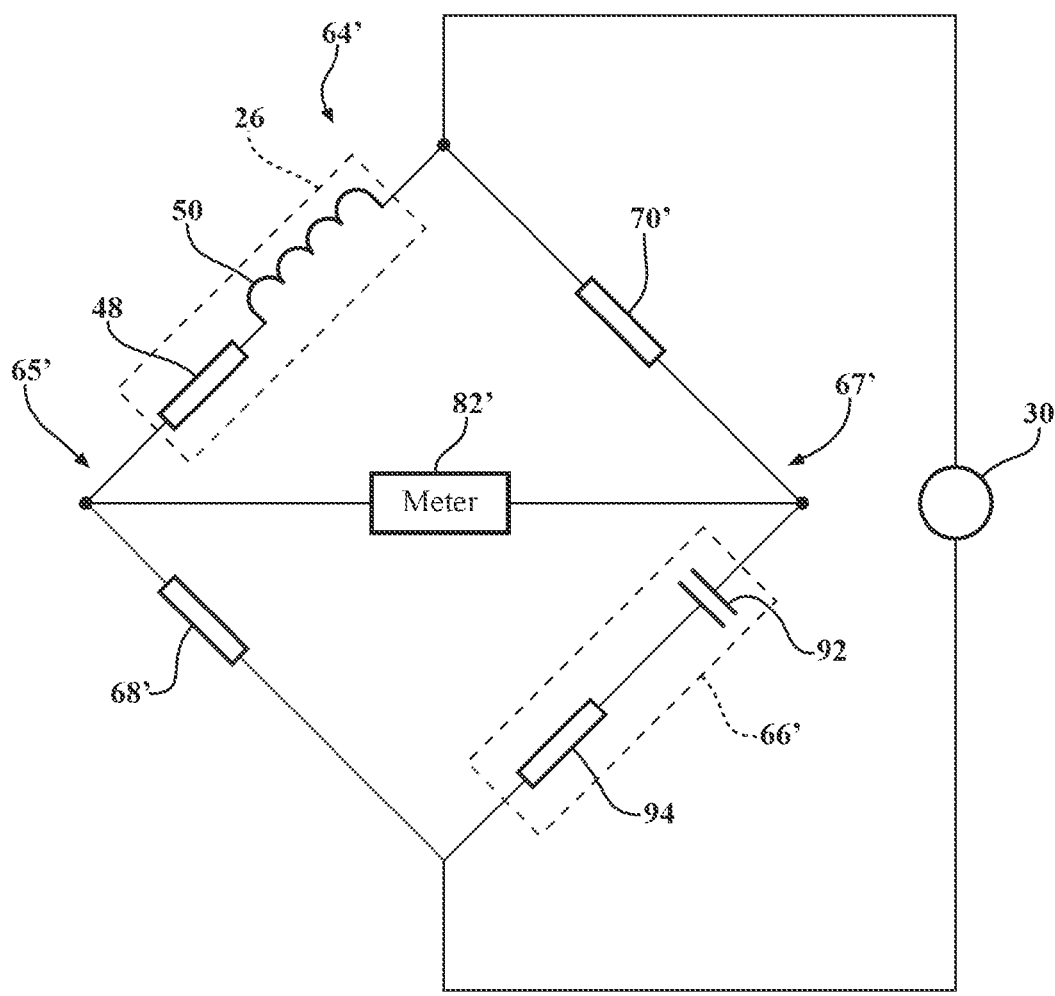
FIG. 7 is a schematic view illustrating an alternative bridge circuit for evaluating the condition of a laminated core with reference to a reference element.

Referring to FIG. 7, an alternative bridge circuit 64' incorporating an alternative reference element 66' is illustrated, and is configured as a Maxwell-Wein bridge circuit. In this configuration, as with the previous configuration, the reference element 66' is separate from the laminated core 12. The first upper arm of the first branch 65' of the bridge circuit 64' is formed by the probe structure 27. The reference element 66' may comprise a capacitor 92 and a resistor 94, or may comprise only the capacitor 92, and defines the second lower arm in the second branch 67' of the bridge circuit 66'. In the event that the reference element 66' comprises both the capacitor 92 and the resistor 94, the capacitor 92 and resistor 94 may be configured either in series, as shown, or in parallel. The first lower arm 68' and the second upper arm 70' may comprise components that are the same as, or similar to, those described for the arms 68, 70 with reference to FIGS. 6A, 6B, and 6C. Since the phase shifts associated with the inductance 50 in the winding 26 of the probe structure 27 will be opposite from the phase shifts in the capacitor 92, the inductive impedance of the probe structure 27 may be balanced out by the capacitive impedance of the reference element 66' located in the opposite arm of the bridge circuit 64'. In accordance with this aspect, the probe structure 27 may be moved along the laminated core 12 in the longitudinal direction, L, to detect shorts between the laminations. When the probe structure 27 encounters a short 31 (FIG. 1A) in the laminations of the laminated core 12, the impedance of the winding 26 will change relative to the impedance of the reference element 66', changing the balance in the bridge circuit 64', as may be indicated by a change in current or voltage on a meter 82' located between the two branches 65', 67' of the bridge circuit 64'.

Figure 9:
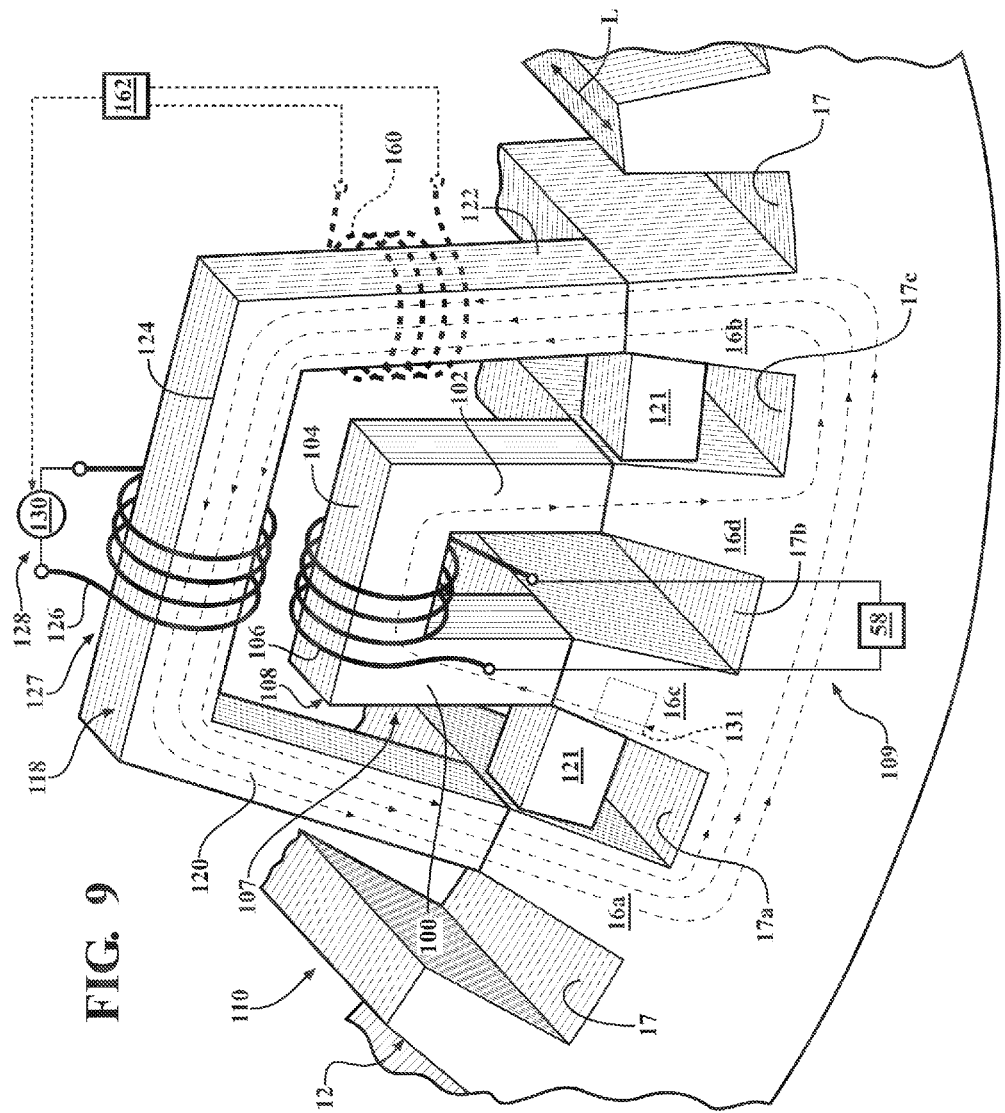
FIG. 9 is a perspective view of an alternative apparatus for evaluating the condition of a laminated core.

Referring to FIG. 9, an alternative apparatus 110 for evaluating the condition of the magnetic circuit of the laminated core 12 is illustrated. The apparatus 110 includes a first probe assembly 127 comprising a first yoke 118 and a first winding 126 wound around the yoke 118 and defining an excitation winding. The first yoke 118 may comprise a U-shaped ferromagnetic member, which may comprise a plurality of laminated sheets, and includes a pair of arms 120, 122 connected by a transverse portion 124. The transverse portion 124 of the yoke 118 may be wound with the first winding 126. During a testing procedure for evaluating the condition of the laminated core 12, the first yoke 118 may be positioned extending between a first pair of teeth 16a, 16b with the pair of arms 120, 122 in engagement with the first pair of teeth 16a, 16b.

The apparatus 110 further includes a second probe assembly 107 comprising a second yoke 108 and a second winding 106 wound around the second yoke 108 and defining a sensing winding. The second yoke 108 may comprise a U-shaped ferromagnetic member, smaller than the first yoke 118, and which may comprise a plurality of laminated sheets. The second yoke 108 includes a pair of arms 100, 102 connected by a transverse portion 104. The transverse portion 104 of the second yoke 108 may be wound with the second winding 106. During a testing procedure for evaluating the condition of the laminated core 12, the second yoke 108 may be positioned extending between a second pair of teeth 16c, 16d with the pair of arms 100, 102 in engagement with the second pair of teeth 16c, 16d. The second pair of teeth 16c, 16d are located intermediate or between the first pair of teeth 16a, 16b. As illustrated in FIG. 9, the first yoke 118 may span across three slots 17a, 17b, 17c, including the second pair of teeth 16c, 16d, and the second yoke 108 may span across the single slot 17b located intermediate or between the other two slots 17a and 17b. Alternatively, the first yoke 118 may span across more than three slots 17, and the second yoke 108 may be located on intermediate teeth to span across slots 17 selected from the slots 17 spanned by the first yoke 118. In general, the second yoke 108 will span at least two fewer slots 17 than the number of slots 17 spanned by the first yoke 118.

The second yoke 108 may be connected or rigidly attached to the first yoke 118, such that the first and second yokes 118, 108 may be moved in unison along the laminated core 12. The second yoke 108 may be aligned in the same plane with the first yoke 118, with the transverse portion 104 of the second yoke 104 located directly below or inwardly from the transverse portion 124 of the first yoke 118. Alternatively, the second yoke 108 may be in close proximity to but slightly offset in the longitudinal direction, L, relative to the first yoke 118, to the extent that the second yoke 108 is still located within a region of the magnetic flux generated by the first probe 127, as is discussed further below.

The probe assembly 127 may be connected to an electrical circuit 128 including a power source 130 to provide an alternating voltage or current to the winding 126 to produce a magnetic flux in a local region of the laminated core near the probe assembly 127. The power source 130 may comprise a power source providing an output as described above for the power source 30 in the apparatus 10 to generate a magnetic flux density the same as or comparable to the magnetic flux density generated in the laminated core 12 during operation of the electric machine.

The second probe assembly 107 may comprise a sensor probe, where a voltage may be produced in the second winding 106 as a result of the second yoke 108 being magnetically linked through the second pair of teeth 16c, 16d to the magnetic flux generated in the laminated core 12 through the first probe assembly 127. That is, the second probe assembly 107 may sense a portion of the flux produced by the first probe assembly 127 as a sensed flux leakage through the second pair of teeth 16c, 16d. A variation in the voltage as the structure comprising the first and second probe assemblies 127, 107 is moved along the laminated core in the longitudinal direction, L, or a particular voltage value relative to a predetermined threshold, measured from the second probe assembly 107 may provide an indication of a fault, i.e., a short, in the laminations of the laminated core 12. The second winding 106 may be located in a second circuit 109 including a monitoring module 158 which may comprise an operator readable meter for monitoring voltage. Alternatively, or in addition, the monitoring module 158 may digitize the results received as an indicator of a fault in the laminated core 12, such as by means of a microprocessor included in the monitoring module 158, and store the digitized results in a memory for automated processing and analysis to identify fault locations in the laminated core 12.

In accordance with a further aspect of the configuration illustrated in FIG. 9, in the event that the testing procedure using the apparatus 110 is performed without generator stator windings present in the slots 17, magnetic shunts 121 may be placed in slots 17a, 17c defined between the first pair of teeth 16a, 16b and the second pair of teeth 16c, 16d, respectively. The shunts 121 may be constructed of a laminated magnetic material, and may be positioned within the slots 17a, 17c to redirect a larger portion of the magnetic flux to the second probe assembly 107. It is believed that the shunts 121, and associated redirection of magnetic flux, may increase the sensitivity of the apparatus 110 to sensing a lamination short in the second pair of teeth 16b, 16c. That is, the shunts 121 may increase the amount of magnetic flux directed into the second pair of teeth 16a, 16b, increasing the strength of a signal associated with a fault in the laminations. Further, the shunts 121 may be moved to different radial positions within the slots 17a, 17b, i.e., to different positions relative to the tips of the teeth 16a, 16b, to facilitate identification of the particular radial location of a lamination short along the teeth 16a, 16b, as exemplified by the diagrammatically depicted lamination short 131.

It should be understood that, although the apparatus 110 is described above with reference to the first winding 126 comprising the excitation winding, and the second winding 106 comprising the sensing winding, the location of the excitation and sensing windings may be switched, such that the second probe 107 operates to provide a magnetic flux to the laminated core 12 and the first probe 127 operates to sense the magnetic flux in the laminated core 12 in order identify the location of a fault in the laminations.

In further aspects of the apparatus 110, the power supply 130 may be operated without special stabilization relative to the current, or may comprise a constant voltage power source. Alternatively, the power source 130 may be controlled such that a constant flux is maintained in the first yoke 118, where the flux in the first yoke may be sensed by a flux sensing winding 160, see FIG. 9, connected to a voltage regulator 162 for controlling a voltage output of the power supply 130. The magnetic flux in the first yoke 118 generates an AC voltage in the flux sensing winding 160 that is proportional to the magnetic flux in the yoke 118. The regulator 162 may monitor the output AC voltage of the flux sensing winding 160 to automatically control the output voltage of the power source 130 so as to maintain the magnetic flux in the yoke 118 substantially constant.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of evaluating the condition of a laminated core of an electric machine, comprising:
   positioning a magnetic flux injection excitation yoke extending between a pair of teeth of the laminated core, the excitation yoke having a pair of arms in engagement with the pair of teeth, and the excitation yoke being wound with an excitation winding for producing a magnetic flux excitation;
   supplying power to an electrical circuit defined by the excitation winding to produce a magnetic flux in the excitation yoke and to form a magnetic circuit through the excitation yoke and the laminated core;
   measuring a characteristic of the electrical circuit of the excitation winding to identify a fault in the magnetic circuit corresponding to an eddy current between individual laminations in the laminated core; and
   wherein measuring the characteristic of the electrical circuit of the excitation winding includes determining a variation in the characteristic in the excitation winding corresponding to the fault in the magnetic circuit relative to a determination of the same characteristic measured in the excitation winding for a magnetic circuit created through the excitation yoke and a portion of the laminated core without a fault.

2. The method of claim 1, wherein measuring the characteristic of the electrical circuit includes determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

3. The method of claim 1, wherein supplying power to the excitation winding comprises providing power to the excitation winding at a constant voltage.

4. The method of claim 3, wherein measuring the characteristic of the electrical circuit includes determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

5. The method of claim 1, wherein supplying power to the excitation winding comprises providing power to the excitation winding at a constant current.

6. The method of claim 5, wherein measuring the characteristic of the electrical circuit includes determining a variation in at least one of an impedance of the excitation winding and a voltage applied to the excitation winding corresponding to the fault in the magnetic circuit relative to a corresponding characteristic measured in the excitation winding for a magnetic circuit created through the excitation yoke and a portion of the laminated core without a fault.

7. The method of claim 1, wherein the excitation yoke includes a second winding, and supplying power to the excitation winding comprises measuring a voltage in the second winding corresponding to the magnetic flux in the excitation yoke and adjusting a voltage applied to the excitation winding with reference to the voltage in the second winding to maintain a constant magnetic flux in the excitation yoke.

8. The method of claim 7, wherein measuring the characteristic of the electrical circuit includes determining a variation in at least one of an impedance of the excitation winding and a current in the excitation winding corresponding to the fault in the magnetic circuit relative to a corresponding characteristic measured in the excitation winding for a magnetic circuit created through the excitation yoke and a portion of the laminated core without a fault.

9. The method of claim 1, including a reference element having an output characteristic corresponding to the measured characteristic of the excitation winding, and the characteristic of the excitation winding is compared to the output characteristic of the reference element to identify the fault in the magnetic circuit.

10. The method of claim 9, wherein the electrical circuit of the excitation winding comprises a bridge circuit in which the excitation winding and the reference element are each located in a respective branch of the bridge circuit.

11. The method of claim 10, wherein the reference element includes a reference yoke wound with a reference winding, and the reference winding is connected to the bridge circuit.

12. The method of claim 11, wherein the reference yoke is located a predetermined distance from the excitation yoke and is moved along the laminated core with the excitation yoke to provide a fault indication at different locations along the laminated core.

13. The method of claim 11, wherein the reference yoke is located at a fixed location and spans between a pair of teeth of the laminated core at a location known to be free of defects between laminations of the laminated core to include the laminated core in a magnetic circuit of the reference yoke.

14. The method of claim 11, wherein the reference yoke is located in a magnetic circuit at a location spaced from the laminated core.

15. The method of claim 10, wherein the reference element includes a capacitor.

16. A method of evaluating the condition of a laminated core of an electric machine, comprising:

positioning a magnetic flux injection excitation yoke extending between a pair of teeth of the laminated core, the excitation yoke having a pair of arms in engagement with the pair of teeth, and the excitation yoke being wound with an excitation winding for producing a magnetic flux excitation;

providing a reference element having an impedance that is the same as an impedance of the excitation winding;

providing a bridge circuit in which the excitation winding and the reference element are each located in a respective branch of the bridge circuit;

supplying power to the excitation winding to produce a magnetic flux in the excitation yoke and to form a magnetic circuit through the excitation yoke and the laminated core, wherein one of a current and a voltage in the branches of the bridge circuit are balanced when the excitation yoke is positioned at a location where there are no faults in the laminated core; and determining an imbalance between the branches of the bridge circuit when at least one of the excitation yoke and the reference element is located adjacent to a fault formed by a short between adjacent laminations in the laminated core.

17. The method of claim 16, wherein the bridge circuit comprises a Maxwell-Wein bridge circuit and the reference element includes a capacitor providing a capacitive impedance balanced against an inductance of the excitation coil.

18. The method of claim 16, wherein the reference element includes a reference yoke wound with a reference winding, and the reference winding is connected to the bridge circuit.

19. The method of claim 18, wherein the reference yoke includes a pair of arms located in engagement with a pair of teeth of the laminated core to form a magnetic circuit through the reference yoke and the laminated core.

20. The method of claim 18, wherein the reference yoke is located in a magnetic circuit separate from the laminated core.

* * * * *